(12) United States Patent
Zhao et al.

(10) Patent No.: US 10,906,018 B2
(45) Date of Patent: Feb. 2, 2021

(54) METHOD FOR THE ENCAPSULATION OF SUBSTANCES IN SILICA-BASED CAPSULES AND THE PRODUCTS OBTAINED THEREOF

(71) Applicant: DWI-LEIBNIZ-INSTITUT FÜR INTERAKTIVE MATERIALIEN E.V., Aachen (DE)

(72) Inventors: Yongliang Zhao, Aachen (DE); Martin Möller, Aachen (DE); Xiaomin Zhu, Aachen (DE)

(73) Assignee: DWI - LEIBNIZ-INSTITUT FÜR INTERAKTIVE MATERIALIEN E.V.

( * ) Notice: Subject to any disclaimer, the term of this patent is extended or adjusted under 35 U.S.C. 154(b) by 234 days.

(21) Appl. No.: 15/741,820

(22) PCT Filed: Jul. 5, 2016

(86) PCT No.: PCT/EP2016/001150
§ 371 (c)(1),
(2) Date: Jan. 4, 2018

(87) PCT Pub. No.: WO2017/016636
PCT Pub. Date: Feb. 2, 2017

(65) Prior Publication Data
US 2018/0200689 A1    Jul. 19, 2018

(30) Foreign Application Priority Data

Jul. 30, 2015    (EP) .................................... 15002261

(51) Int. Cl.
| | | |
|---|---|---|
| *A61K 8/11* | (2006.01) | |
| *B01J 13/18* | (2006.01) | |
| *A61K 8/25* | (2006.01) | |
| *C08L 83/12* | (2006.01) | |
| *C08L 83/06* | (2006.01) | |
| *A61Q 19/00* | (2006.01) | |
| *C08F 2/18* | (2006.01) | |
| *C08F 20/14* | (2006.01) | |
| C08G 77/18 | (2006.01) | |
| C08G 77/46 | (2006.01) | |
| F28D 20/02 | (2006.01) | |

(52) U.S. Cl.
CPC ............... *B01J 13/185* (2013.01); *A61K 8/11* (2013.01); *A61K 8/25* (2013.01); *A61Q 19/00* (2013.01); *C08F 2/18* (2013.01); *C08F 20/14* (2013.01); *C08L 83/06* (2013.01); *C08L 83/12* (2013.01); *A61K 2800/10* (2013.01); *A61K 2800/412* (2013.01); *C08G 77/18* (2013.01); *C08G 77/46* (2013.01); *F28D 20/023* (2013.01)

(58) Field of Classification Search
CPC ........ A61K 8/11; A61K 8/25; A61K 2800/10; A61K 2800/412; A61Q 19/00; B01J 13/185; C08F 2/18; C08F 20/14; C08L 83/06; C08L 83/12; C08G 77/18; C08G 77/46; F28D 20/023
See application file for complete search history.

(56) References Cited

U.S. PATENT DOCUMENTS

| | | |
|---|---|---|
| 6,303,149 B1 | 10/2001 | Magdassi et al. |
| 6,337,089 B1 | 1/2002 | Yoshioka |

FOREIGN PATENT DOCUMENTS

| | | |
|---|---|---|
| EP | 1576035 A1 | 9/2005 |
| JP | 1999-221459 A | 8/1999 |
| JP | 2000225332 A | 8/2000 |
| WO | 2007037202 A1 | 4/2007 |
| WO | 2008028640 A2 | 3/2008 |

OTHER PUBLICATIONS

Self-Templating Amphiphilic Polymer Precursors for Fabricating Mesostructured Silica Particles: A Water-Based Facile and Universal Method, Wang et al., Advanced Materials, Feb. 1013.*
International Search Report and Written Opinion, dated Oct. 17, 2016; International Application No. PCT/EP2016/001150, filed Jul. 5, 2016. ISA/EP.
Japanese Office Action dated Nov. 26,2019; Japanese Patent Application No. 2018-524531.

* cited by examiner

*Primary Examiner* — Irina S Zemel
(74) *Attorney, Agent, or Firm* — McDonald Hopkins LLC

(57) ABSTRACT

The present invention relates to a method for enclosing either hydrophobic or hydrophilic substances in silica-based micro- and nanocapsules via emulsion techniques. More specifically, it relates to a method for the preparation of 0.01-100 μm, particularly 0.01-10 μm, silica-based microcapsules containing up to 99% (w/w) payload using a silica precursor polymer, polyalkoxysiloxane (PAOS), preferentially polyalkylalkoxysiloxane (R-PAOS), which acts not only as a silica source but also an emulsifier. In order to obtain mechanically stable capsules, the conversion of PAOS or R-PAOS is accompanied with the solidification of the organic phase. For the encapsulation of hydrophobic substances, oil-in-water emulsions are formed. The formation of water-in-oil-in-water double emulsions is required to encapsulate hydrophilic compounds.

15 Claims, 4 Drawing Sheets

METHOD FOR THE ENCAPSULATION OF SUBSTANCES IN SILICA-BASED CAPSULES AND THE PRODUCTS OBTAINED THEREOF

CROSS-REFERENCE TO RELATED APPLICATION

This application is a 35 U.S.C. 371 national stage filing of PCT Application No. PCT/EP2016/001150 filed on Jul. 5, 2016, entitled "METHOD FOR THE ENCAPSULATION OF SUBSTANCES IN SILICA-BASED CAPSULES AND THE PRODUCTS OBTAINED THEREOF," which claims priority to European Patent Application No. 15002261.4, filed on Jul. 30, 2015, each of which are incorporated herein in their entirety by reference.

The present invention relates to a method for enclosing either hydrophobic or hydrophilic substances in silica-based micro- and nanocapsules via emulsion techniques. More specifically, it relates to a method for the preparation of 0.01-100 µm, particularly 0.01-10 µm, silica-based microcapsules containing up to 99% (w/w) payload using a silica precursor polymer, polyalkoxysiloxane (PAOS), preferentially polyalkylalkoxysiloxane (R-PAOS), which acts not only as a silica source but also an emulsifier. In order to obtain mechanically more stable capsules, the conversion of PAOS or R-PAOS is accompanied with the solidification of the organic phase. For the encapsulation of hydrophobic substances, oil-in-water emulsions are formed. The formation of water-in-oil-in-water double emulsions is required to encapsulate hydrophilic compounds.

Microcapsules are hollow tiny particles consisting of a solid shell that surrounds a core-forming space available to entrap substances. Microencapsulation finds numerous applications in various fields ranging from food and cosmetics to pharmacy and medicine, implementing protection and controlled release of active substances.

Organic polymers are the most widely used shell materials, and the industrial processes for encapsulating active substances into polymer microcapsules include interfacial polymerization, extrusion, coacervation, spray-drying, etc. (for more details see: Lakkis, J. M., Encapsulation and Controlled Release Technologies in Food Systems. 1st ed.; Blackwell: Ames, 2007).

Silica is a promising alternative to organic capsule materials owing to its chemical inertness, mechanical stability, biocompatibility, optical transparency and easy functionalization. Sol-gel technology which combines the control of composition and microstructure at the molecular level with the ability to shape the material to particles, fibers, and thin films under mild and low-energy conditions, is a well-established method for the encapsulation of different substances within a silica shell (for more details see: Pagliaro, M., Silica-Based Materials for Advanced Chemical Applications, The Royal Society of Chemistry, Cambridge, 2009; Ciriminna, R.; Sciortino, M.; Alonzo, G.; de Schrijver, A.; Pagliaro, M., From Molecules to Systems: Sol-Gel Microencapsulation in Silica-Based Materials. *Chem. Rev.* 2011, 111, 765-789). In practice, organic molecules are entrapped in the inner porosity of a silica-based matrix by simply adding the dopant molecules at the onset of the sol-gel process. Low molecular silanes like tetraalkoxysilanes and alkyltrialkoxysilanes were used as the monomers to be condensed to the silica-based matrix.

To entrap substances in silica microcapsules the sol-gel technology is generally combined with emulsions including mini- and micro-emulsions as soft templates to prepare capsular structures. In this case silica is formed at the interface between the oil and water phases, and the dispersed aqueous or oil phase can be encapsulated. For the stabilization of emulsions, surfactants are normally added. For example, U.S. Pat. No. 6,303,149 B1 describes the formation of silica capsules containing organic substances by the combination of oil-in-water emulsions and sol-gel technology in the presence of surfactants. The use of surfactant-stabilized water-in-oil emulsions to prepare silica-based microcapsules was described e.g. in Barbé, C. J.; Kong, L.; Finnie, K. S.; Calleja, S.; Hanna, J. V.; Drabarek, E.; Cassidy, D. T.; Blackford, M. G., Sol-Gel Matrices for Controlled Release: From Macro to Nano Using Emulsion Polymerization. *J. Sol-Gel Sci. Technol.* 2008, 46, 393-410. In order to form nanosized emulsion droplets and subsequently nanocapsules, the surfactant concentration should be very high, but their complete removal is often problematic. Solid particles can also be employed instead of traditional surfactant molecules to stabilize emulsions due to their interfacial activity (Pickering, S. U., *J. Chem. Soc., Trans.* 1907, 91, 2001-2021; Ramsden, W., *Proc. R. Soc. Lond.* 1903, 72, 156-164). These so-called Pickering emulsions can be used to create hollow structures named colloidosomes by fixing the stabilizing colloidal particles at the interface. Microsized all-silica colloidosomes enclosing an aqueous or oil phase were obtained by gluing silica nanoparticles at the water-oil interface using PAOS in water-in-oil or oil-in-water Pickering emulsions, respectively (Wang, H. L.; Zhu, X. M.; Tsarkova, L.; Pich, A.; Möller, M., All-Silica Colloidosomes with a Particle-Bilayer Shell. *ACS Nano* 2011, 5, 3937-3942; Zhao, Y. L.; Li, Y. Q.; Demco, D. E.; Zhu, X. M.; Möller, M., Microencapsulation of Hydrophobic Liquids in Closed All-Silica Colloidosomes. *Langmuir* 2014, 30, 4253-4261). In EP 2 832 691 A1 a process for the preparation of silica nanocapsules in an oil-in-water emulsion using PAOS as the silica precursor is disclosed, where the emulsion is stabilized by PAOS and silica nanoparticles that also catalyze the conversion of PAOS into silica. Silica microcapsules can also be prepared from emulsions without any surfactant by using a two-step sol-gel process (acid-catalyzed hydrolysis and base-catalyzed condensation) in an emulsified mixture (Radin, S.; Chen, T.; Ducheyne, P., The Controlled Release of Drugs from Emulsified, Sol Gel Processed Silica Microspheres. *Biomaterials* 2009, 30, 850-858). In this process an aqueous silica sol prepared from tetraethoxysilane containing active substances is emulsified in a hydrophobic liquid, so it is suitable only for hydrophilic water-dispersible substances. The size of the resulting silica particles is mostly above 10 µm, and is mainly dependent on the speed of stirring during emulsification. Furthermore, no information regarding the internal morphology of these particles is available. Most probably, the substances were encapsulated in the silica matrix, i.e. no core-shell structure was formed.

PAOS was so far used only as a silica precursor to generate sol-gel silica. For example, WO 2007/037202 discloses a silica-combined polymer particle comprising a polymer ingredient derived from a polymerizable vinyl monomer and a silica ingredient, wherein the silica ingredient is a condensate derived from a PAOS oligomer inert to the polymerizable vinyl monomer. U.S. Pat. No. 6,337,089 discloses a microcapsule containing core material and a capsule wall, in which the capsule wall of the microcapsule comprises organosilicone resin formed from a hydrolytic condensate of organosilanes containing hydroxyl-groups. JP 2000-225332 discloses a membrane wall formed from the hydrolytic condensate of organosilanes containing hydroxyl-groups.

The object underlying the present invention is to provide an improved straightforward method for the preparation of silica-based micro- and nanocapsules.

This object and others, which will become apparent from the following disclosure, are achieved by the following embodiments characterized in the accompanying claims.

In a first embodiment, the present invention relates to a process for the preparation of silica-based micro- and nanocapsules loaded with up to 99% (w/w) hydrophobic organic liquid compounds, comprising the step of:

emulsifying a hydrophobic, water insoluble liquid comprising (i) PAOS or amphiphilic PAOS that are partially substituted with hydrophilic groups and (ii) a hydrophobic organic liquid in an aqueous solution, without additional surfactants and without any preformed (nano)particles like silica nanoparticles, under shearing forces for a time period sufficient to form the silica-based capsules.

Examples of the hydrophobic organic liquids, which can be used in said first embodiment, are alkanes (cf. Example 1), alkenes, alkynes, esters, ethers, ketones, aldehydes, aromatic compounds, polymers (cf. Example 2), etc.

U.S. Pat. No. 6,337,089 and JP 2000-225332, as mentioned above, both disclose a process for the preparation of capsules from organosilicone (silicone resin) containing at least one non-hydrolyzable organic group, whereas the present invention is directed to inorganic $SiO_2$ capsules. Moreover, the resin precursor is synthesized and dispersed in water. To the contrary, PAOS used in the present invention is hydrophobic, it is applied from the organic phase.

In order to obtain mechanically more stable capsules, the conversion of PAOS or R-PAOS is accompanied with the solidification of the organic phase.

In a second embodiment, the present invention relates to a process for the preparation of silica-based micro- and nanocapsules loaded with up to 99% (w/w) hydrophobic, water insoluble polymers, comprising the steps of:

a) emulsifying a hydrophobic, water insoluble solution comprising (i) PAOS, (ii) radically polymerizable hydrophobic organic monomers and (iii) an initiator in an aqueous solution under shearing forces without additional surfactants and without any preformed (nano)particles like silica nanoparticles; and b) heating the resulting emulsion to a higher temperature to induce the polymerization for a time period sufficient to form the silica-based capsules, c) cooling the mixture down to room temperature, and d) isolating the thus obtained polymer@$SiO_2$ capsules.

This embodiment (second embodiment) can be of particular interest for the coating industry, since such core-shell particles were used as a key component for the preparation of antireflective coatings (WO2008/028640 A2).

In this second embodiment, optionally non-(co)polymerizable hydrophobic organic compounds, which can turn into a liquid form at the emulsification temperature, can additionally be added in step a). When using styrene as the radically polymerizable hydrophobic organic monomer, silica-based micro- and nanocapsules can be obtained where non-(co)polymerizable hydrophobic organic compounds are then encapsulated in the polystyrene@$SiO_2$ core-shell micro- and nanocapsules (cf. Example 6). The non-(co)polymerizable hydrophobic compounds are selected from alkanes, esters, ethers, ketones, aldehydes, aromatic compounds, polymers and etc.

While WO 2007/037202 discloses a silica-combined polymer particle comprising a polymer ingredient derived from a polymerizable vinyl monomer and a silica ingredient, it describes a respective manufacturing process which requires preformed particles to stabilize the emulsion. To the contrary, in the present invention the emulsions are stabilized by PAOS only. According to the present invention, a silica precursor polymer, PAOS, is utilized as a sole emulsion stabilizer due to its water insolubility and at the same time pronounced amphiphilicity induced by hydrolysis at the oil/water interface.

In a third embodiment, the present invention relates to a process for the preparation of silica-based micro- and nanocapsules loaded with up to 99% (w/w) crystallizable at room temperature hydrophobic, water-insoluble substances, comprising the steps of:

a) emulsifying a hydrophobic, water insoluble mixture comprising (i) PAOS and (ii) an at room temperature crystallizable, hydrophobic organic compound in an aqueous solution under shearing forces at a temperature above the melting temperature of the crystallizable organic material without additional surfactants and without any preformed (nano)particles like silica nanoparticles, and b) subsequently heating the emulsion obtained in step a) for a time period sufficient to form the silica-based capsules, c) cooling the mixture down to room temperature, and d) isolating the thus obtained crystallizable, hydrophobic organic compound@$SiO_2$ capsules.

At room temperature (i.e. ca. 23° C.) crystallizable, hydrophobic organic compounds (solids) that are meltable at high temperature include waxes, e.g. alkanes, esters of alkyl alcohols and alkyl carboxylic acids, or their mixtures. This embodiment (second embodiment) is of particular interest for the cosmetic industry where waxes are widely employed as an important cosmetic ingredient. Using this technique the hydrophobic waxes can be turned to be hydrophilic; hence the formulation possibility can be significantly broadened. Furthermore, the waxes are organic phase change materials; the microencapsulation improves their processability, e.g. the ability to form composite materials with polymer matrices, and reusability. For example, docosane and myristyl myristate can be mentioned here (cf. Examples 8 and 9). In this case, the encapsulation reaction is conducted at a temperature above the melting temperature of the solids. After the condensation reaction is over, the system is cooled down to room temperature.

Optionally hydrophobic organic compounds such as alkanes, alkenes, alkynes, esters, ethers, ketones, aldehydes, aromatic compounds, polymers like e.g. poly(dimethylsiloxane) PDMS, etc. that are in a liquid form at the emulsification temperature can additionally be added in step a), i.e. in the form of a mixture with the at room temperature crystallizable, hydrophobic organic compound (solids); cf. Example 10. This option is of particular interest for the cosmetic industry, since the hydrophobic organic compounds can be organic fragrances and flavours.

Optionally, also a polymer such as PDMS can be added in step a), besides PAOS and the at room temperature crystallizable, hydrophobic organic compound, leading to PDMS@crystallizable, hydrophobic organic compound@$SiO_2$ capsules; cf. Example 11. PDMS is widely used in cosmetics e.g. for skin protection.

In a fourth embodiment, the present invention relates to a process for the preparation of silica-based micro- and nanocapsules loaded with up to 95% (w/w) hydrophilic, water soluble substances, comprising the steps of:

a) emulsifying an aqueous solution containing hydrophilic, water soluble substances in a hydrophobic, water insoluble solution comprising (i) PAOS, (ii) radically polymerizable hydrophobic organic monomers and (iii) an initiator under shearing forces without additional surfactants and without any preformed (nano)particles like silica nanoparticles, b) emulsifying the water-in-oil emulsion of step a) in an aqueous solution under shearing forces without additional surfactants and without any preformed (nano)particles like silica nanoparticles, c) heating the emulsion of step b) to a higher temperature to induce the polymerization for a time period sufficient to form the silica-based capsules, d) cooling the mixture down to room temperature, and e) isolating the thus obtained silica-based capsules.

In this fourth embodiment the aqueous solution containing hydrophilic, water soluble substances can also be pure water, i.e. $H_2O$ itself (cf. Example 13) or any aqueous solutions containing e.g. peroxides, salts, vitamins, peptides, dyes, carbohydrates (cf. Example 14), etc.

Optionally, non-(co)polymerizable hydrophobic organic compounds, which can turn into a liquid form at the emulsification temperature, can additionally be added in step a) or b) of this fourth embodiment. Thus, these substances are incorporated into the polymer layer of the capsules. The non-(co)polymerizable hydrophobic compounds can be alkanes, esters, ethers, ketones, aldehydes, aromatic compounds, or polymers, etc.

In a fifth embodiment, the present invention relates to a process for the preparation of silica-based micro- and nanocapsules loaded with up to 95% (w/w) hydrophilic, water soluble substances, comprising the steps of:

a) emulsifying an aqueous solution containing hydrophilic, water soluble substances in a hydrophobic, water insoluble mixture comprising (i) PAOS, (ii) molten organic compounds that crystallize at room temperature under shearing forces at a temperature above the melting temperature of the crystallizable organic material without additional surfactants and without preformed (nano)particles like silica nanoparticles, b) emulsifying the water-in-oil emulsion of step a) in an aqueous solution at a temperature above the melting temperature of the crystallizable organic material without additional surfactants and without any preformed (nano)particles like silica nanoparticles, c) subsequently heating the emulsion obtained in step b) for a time period sufficient to form the silica-based capsules, d) cooling the mixture down to room temperature, and e) isolating the thus obtained silica-based capsules.

Optionally, one or more hydrophobic organic compounds, which can turn into a liquid form at the emulsification temperature, can additionally be added in step a) or b). Thus, these substances are incorporated into the wax layer of the capsules. The hydrophobic compounds can be alkanes, alkenes, alkynes, esters, ethers, ketones, aldehydes, aromatic compounds, or polymers, etc.

The processes of the present invention enable to obtain mechanically stable 0.01-100 µm silica-based microcapsules enclosing either hydrophobic or hydrophilic substances using silica precursor polymers, PAOS or R-PAOS, as silica sources and simultaneously as stabilizers of emulsions without any additional surfactant or preformed (nano)particles but in combination with (partial) solidification of the organic phase.

Preferentially, the present invention allows preparation of capsules with a diameter less than 10 µm, preferably less than 0.6 µm with a size variation less than 20% with up to 100% encapsulation efficiency and up to 99% (w/w) payload. Encapsulation of a hydrophobic payload exploits polyalkoxysiloxane (PAOS), preferentially polyalkylalkoxysiloxane (R-PAOS), as a silica precursor preferentially in combination with a solidification process of the hydrophobic organic phase. Within the first step PAOS or R-PAOS acts as an efficient emulsifier as well as the source for the formation of a silica shell around the organic microdroplets. Ageing of the resulting dispersion systems at a certain temperature and a suitable pH value of the aqueous phase stabilizes the core-shell structure. The solidification process can be caused by polymerization, vitrification or crystallization. Resulting microcapsules are dispersed in water in a stable form, and can be isolated in a powder form, and afterwards be re-dispersed in water.

For the encapsulation of hydrophilic compounds, their aqueous solution is first emulsified in the organic phase containing PAOS or R-PAOS, and the resulting oil-in-water emulsion is then dispersed in water to result in a water-in-oil-in-water double emulsion. After ageing, the aqueous solution of the hydrophilic compounds is entrapped in the silica-based capsules. In addition, hydrophobic organic substances can be simultaneously encapsulated in the organic phase of the capsules.

The processes of the present invention are based on the formation of oil-in-water emulsions of a hydrophobic mixture that is comprised of PAOS or R-PAOS, hydrophobic substances to be loaded, and preferentially polymerizable or crystallizable hydrophobic compounds in an aqueous solution, or water-in-oil-water emulsions containing the water soluble substances to be loaded in the inner aqueous phase and a hydrophobic mixture that is comprised of PAOS or R-PAOS, preferentially polymerizable or crystallizable hydrophobic compounds and optionally hydrophobic substances to be loaded. In order to obtain mechanically stable capsules, besides the conversion of PAOS or R-PAOS into silica, the oil phase should preferentially be (partially) solidified by polymerization or crystallization.

Usually, the pH of the outer continuous aqueous solution lies in the range of 1-12, more preferably 3-11, even more preferably 4-10.

PAOS are partially condensed products of tetraalkoxysilane that can be polymethoxysiloxanes, polyethoxysiloxanes, polypropoxysiloxanes, polybutoxysiloxanes etc. or with mixed alkoxy groups. Some of them are commercially available, for example polyethoxysiloxane with silica content 40% (w/w) (SE40), polyethoxysiloxane with silica content 48% (w/w) (SE48) and polymethoxysiloxanes with silica content 53% (w/w) (ME53). PAOS can also be synthesized according to the literature procedures (Abe, Y.; Shimano, R.; Arimitsu, K.; Gunji, T., Preparation and Properties of High Molecular Weight Polyethoxysiloxanes Stable to Self-Condensation by Acid-Catalyzed Hydrolytic Polycondensation of Tetraethoxysilane. *J. Polym. Sci., Part A: Polym. Chem.* 2003, 41, 2250-2255, DE 10261289 A1 or Zhu, X. M.; Jaumann, M.; Peter, K.; Möller, M.; Melian, C.; Adams-Buda, A.; Demco, D. E.; Blümich, B., One-Pot Synthesis of Hyperbranched Polyethoxysiloxanes. *Macromolecules* 2006, 39, 1701-1708). PAOS may contain two or more types of alkoxy groups, for example polyethoxysiloxane substituted partially with poly(ethylene glycol) monomethyl ether described in Wang, H.; Agrawal, G.; Tsarkova, L.; Zhu, X. M.; Möller, M., Self-Templating Amphiphilic Polymer Precursors for Fabricating Mesostructured Silica Particles: A Water-Based Facile and Universal Method. *Adv. Mater.* 2013, 25, 1017-1021.

R-PAOS are prepared by co-condensation of tetraalkoxysilane with alkyltrialkoxysilane and/or dialkyldialkoxysilane.

PAOS or R-PAOS as used in the present invention, have preferably a molecular weight in the range of 500-20000 and the silica content in the range of 40-60% (w/w).

Different oil-in-water or water-in-oil-in-water emulsions are stabilized either by amphiphilic PAOS or R-PAOS, for example polyethoxysiloxane substituted partially with hydrophilic groups, e.g. poly(ethylene glycol) monomethyl ether, or by PAOS or R-PAOS partially hydrolyzed during the emulsification process.

The substitution degree of amphiphilic PAOS, i.e. PAOS partially substituted with hydrophilic groups, should be adjusted so that the hydrophilic-lipophilic balance (HLB) of the resulting molecule lies in the range of 1-16, more specifically 2-12, and even more specifically 3-10. The HLB value can be calculated as follows.

$$HLB = 20 M_h/M$$

where $M_h$ is the molecular mass of the hydrophilic portion of the molecule, and M is the molecular mass of the whole molecule.

The emulsions are created under appropriate shear forces, using an apparatus such as a sonicator, a microfluidizer, a (high pressure) homogenizer, a stirrer, etc.

The encapsulated substances can be a wide range of hydrophobic substances that include any hydrophobic liquids and any solids that melt into hydrophobic liquids at high temperature. Hydrophobic substances can be either pure compounds or mixtures. The enclosed substances can also be a wide range of hydrophilic compounds, which are water soluble liquid or solids, and can be either pure compounds or mixtures. They are dissolved in water to form an aqueous solution, which is in turn encapsulated.

The polymerizable hydrophobic monomers are any hydrophobic monomers which can be radically polymerized. They can be styrene, methyl styrene, alkyl methacrylates, alkyl acrylates, acrylonitrile, etc. or their mixtures. Monomers with two or more carbon-carbon double bonds such as divinylbenzene, di(meth)acrylates or tri(meth)acrylates can also be added to the monomer mixture.

For the radical polymerization an initiator is added to the monomer mixture. The initiator should be oil-soluble, it can be a thermal initiator, for example, 2,2'-azobis(2-methylpropionitrile) (AIBN), 2,2'-azobis-(2,4-dimethylvaleronitrile), 2,2'-azobis-(2-methylbutyronitrile), benzoyl peroxide, etc. or a photoinitiator like acetophenone, anisoin, benzoin alkyl ether, etc. To initiate the radical polymerization, the emulsions should be heated or irradiated by UV light.

In the processes according to the present invention the heating can last from 1 h to 3 days.

The loaded silica capsules can be isolated by centrifugation or filtration and subsequent drying.

As mentioned, the particle size of the final product can be controlled in the range of 0.01-100 µm, more preferentially 0.01-10 µm, even more preferentially 0.01-0.6 µm. The particles obtained by the present processes have good mechanical strength. They can sustain high shear forces, e.g. under ultrasonication, maintaining the encapsulation properties and particle size distribution. The particles can also be calcined at a temperature above 500° C. such that the organic core is removed resulting in hollow silica particles. Thus, the payload of the encapsulated substances in the silica capsules may be from zero up to 99% weight, in cases where double emulsions are involved (cf. fourth and fifth embodiments) up to 95% weight.

Figure 1:
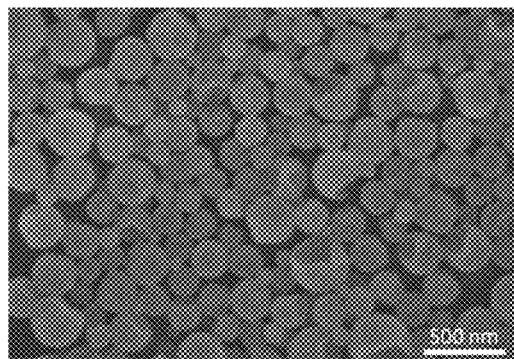
FIG. 1. FE-SEM micrograph of dried hexane@$SiO_2$ nanocapsules prepared in Example 1.
Figure 2:
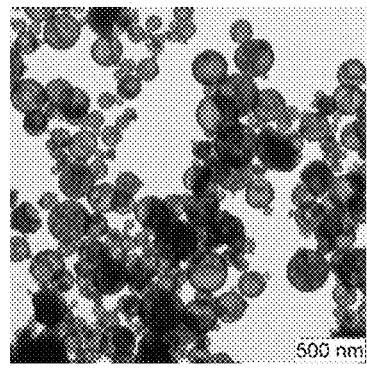
FIG. 2. TEM micrograph of dried hexane@$SiO_2$ nanocapsules prepared in Example 1.
Figure 3:
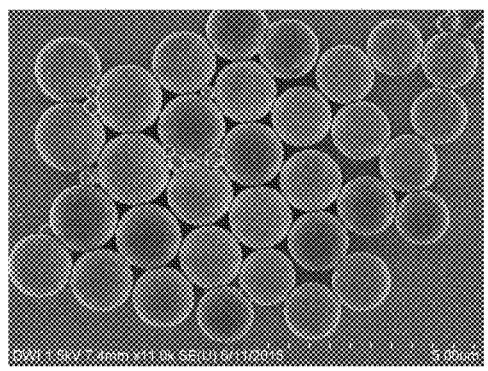
FIG. 3. FE-SEM micrograph of poly(dimethylsiloxane)@$SiO_2$ capsules prepared in Example 2.
Figure 4:
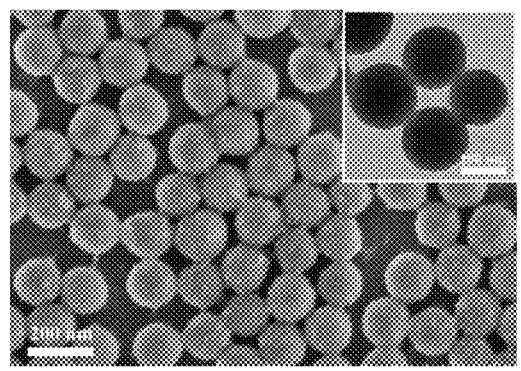
FIG. 4. FE-SEM micrograph of polystyrene@$SiO_2$ core-shell nanoparticles prepared in Example 3. The inset is TEM image of these particles.
Figure 5:
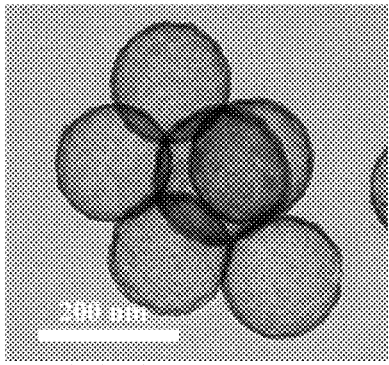
FIG. 5. TEM micrograph of silica hollow nanocapsules prepared after calcination in Example 3.
Figure 6:
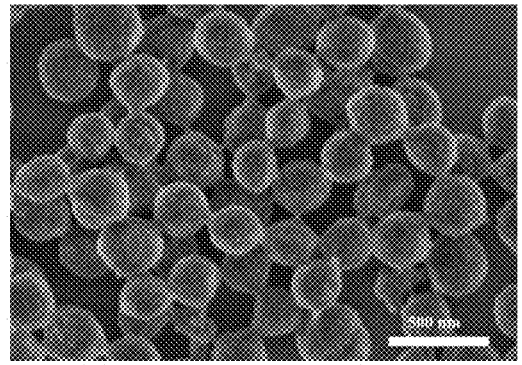
FIG. 6. FE-SEM micrograph of polymethylmethacrylate@$SiO_2$ core-shell nanoparticles prepared in Example 4.
Figure 7:
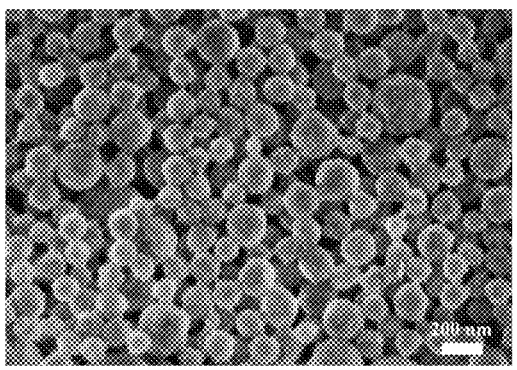
FIG. 7. FE-SEM micrograph of poly(methylmethacrylate-co-styrene)@$SiO_2$ core-shell nanoparticles prepared in Example 5.
Figure 8:
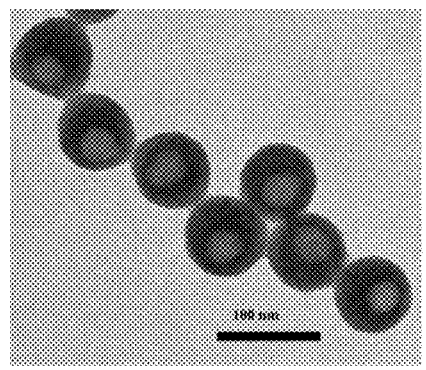
FIG. 8. TEM image of hexadecane@polystyrene@$SiO_2$ nanocapsules prepared in Example 6.
Figure 9:
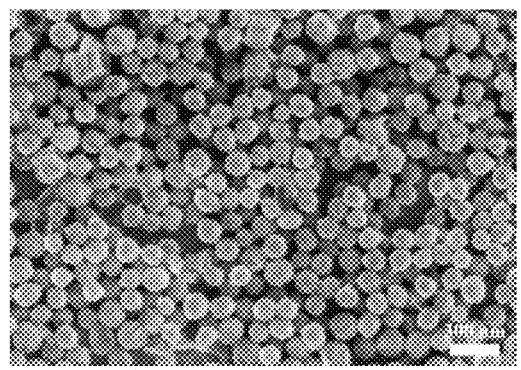
FIG. 9. FE-SEM image of hexyl acetate@polystyrene@$SiO_2$ nanocapsules prepared in Example 7.
Figure 10:
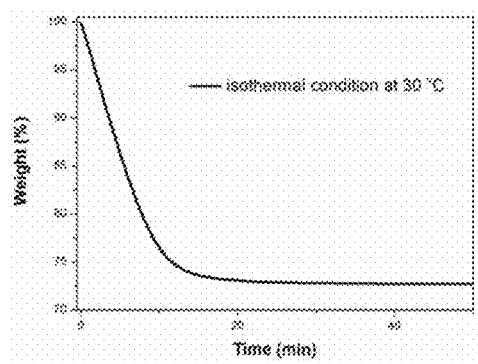
FIG. 10. Isothermal weight loss of hexyl acetate@polystyrene@$SiO_2$ nanocapsules measured at 30° C.
Figure 11:
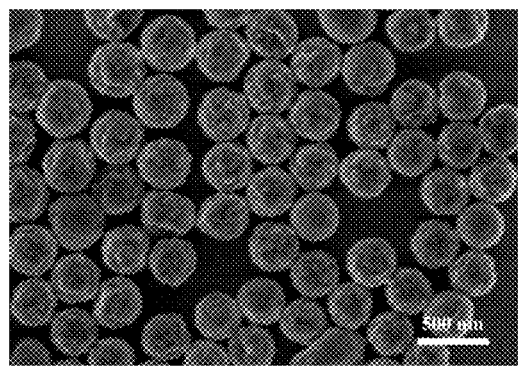
FIG. 11. FE-SEM micrograph of docosane@$SiO_2$ core-shell nanoparticles prepared in Example 8.
Figure 12:
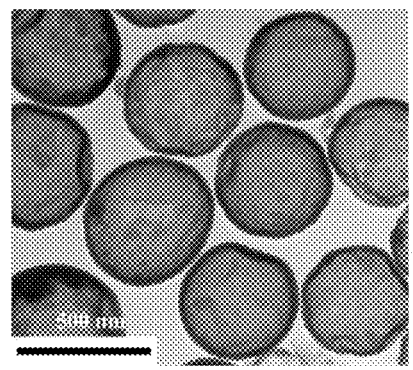
FIG. 12. TEM micrograph of docosane@$SiO_2$ core-shell nanoparticles prepared in Example 8.
Figure 13:
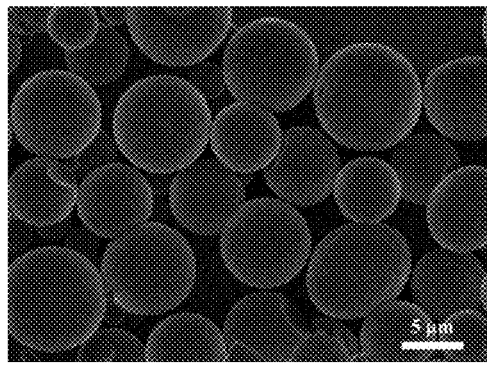
FIG. 13. FE-SEM micrograph of myristyl myristate@$SiO_2$ core-shell particles prepared in Example 9.
Figure 14:
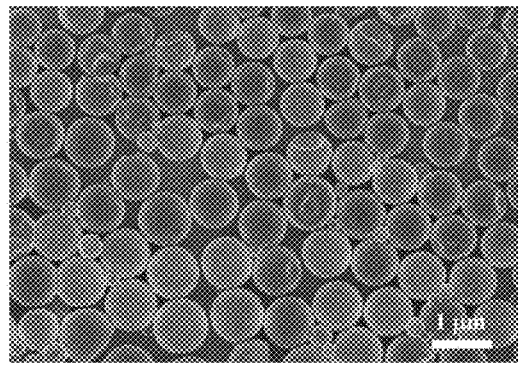
FIG. 14. FE-SEM micrograph of poly(dimethylsiloxane)@docosane@$SiO_2$ core-shell particles prepared in Example 11.
Figure 15:
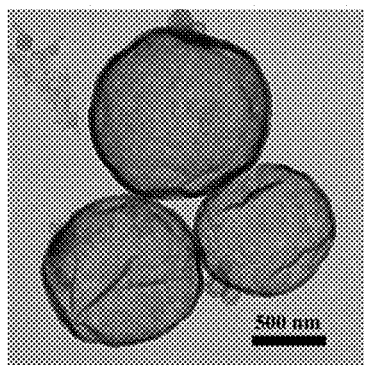
FIG. 15. TEM micrograph of poly(dimethylsiloxane)@docosane@$SiO_2$ core-shell particles prepared in Example 11.
Figure 16:
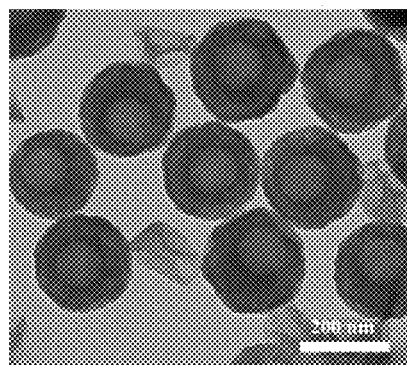
FIG. 16. TEM micrograph of aqueous solution@$SiO_2$@polystyrene@$SiO_2$ capsules prepared in Example 12.

The invention will now be elucidated by way of the following examples without however being limited thereto.

EXAMPLES

PAOS was synthesized according to Zhu, X. M.; Jaumann, M.; Peter, K.; Möller, M.; Melian, C.; Adams-Buda, A.; Demco, D. E.; Blümich, B., One-Pot Synthesis of Hyperbranched Polyethoxysiloxanes. *Macromolecules* 2006, 39, 1701-1708, and the resulting polyethoxysiloxane had a silica content of 49.2% (w/w) and Mn of 1740 g mol$^{-1}$ according to GPC calibrated by polystyrene standards. The other compounds were all obtained from Sigma-Aldrich.

Example 1

1.2 g polyethoxysiloxane where 7% ethoxy groups are substituted with poly(ethylene glycol) monomethyl ether of molecular weight 350 was dissolved in 1.2 g n-hexane. This solution formed spontaneously an emulsion in water. After adjusting the pH of the aqueous solution to 10, an aqueous dispersion of silica nanocapsules containing hexane was obtained.

Example 2

15.0 g polydimethylsiloxane (PDMS) with a viscosity of 10 cSt was added to water of pH 7 heated to 60° C. Afterwards, 15.0 g polyethoxysiloxane was added and the mixture was emulsified with Ultra-Turrax operating at 18000 rpm for 5 minutes at 60° C. The resulting emulsion was stirred at 60° C. for 24 h. The milky dispersion was centrifuged at 11000 rpm. The obtained white solid was rinsed several times with water and then dried. According to electron microscopy data, the size of the resulting PDMS@SiO$_2$ core-shell particles was ca. 1 µm and was narrowly distributed.

Example 3

0.03 g AIBN and 1.2 g polyethoxysiloxane were dissolved in 1.2 g styrene. The solution was emulsified in 30 g water of pH 7 by means of sonication. The resulting emulsion was then heated at 70° C. under nitrogen atmosphere for 24 h. Afterwards, the milky dispersion was centrifuged at 11000 rpm. The obtained white solid was rinsed several times with water and then dried. According to electron microscopy data, the size of the core-shell nanoparticles was ca. 150 nm and was narrowly distributed. The silica shell thickness was ca. 15 nm.

Example 4

0.02 g AIBN and 1.2 g polyethoxysiloxane were dissolved in 1.2 g methylmethacrylate. The solution was emulsified in 30 g water of pH 4 by means of sonication. The resulting emulsion was heated at 65° C. under nitrogen atmosphere for 24 h. The milky dispersion was centrifuged at 11000 rpm. The obtained white solid was rinsed several times with water and then dried. According to electron microscopy data, the size of the core-shell nanoparticles was ca. 300 nm and was narrowly distributed. The silica shell thickness was ca. 30 nm.

Example 5

The synthetic route was similar to that described in Example 2, only instead of 1.2 g methylmethacrylate a mixture of 0.4 g styrene and 0.8 g methylmethacrylate was used. Poly(methylmethacrylate-co-styrene)@SiO$_2$ core-shell nanoparticles were obtained. According to electron microscopy data, the size of the core-shell nanoparticles was ca. 200 nm and was narrowly distributed. The silica shell thickness was ca. 20 nm.

Example 6

The synthetic route was similar to that described in Example 1, only instead of 1.2 g styrene a mixture of 1.2 g styrene and 0.6 g hexadecane was used. Hexadecane was then encapsulated in polystyrene@SiO$_2$ core-shell capsules. According to electron microscopy data, the size of the capsules was ca. 100 nm.

Example 7

The synthetic route was similar to that described in Example 1, only instead of 1.2 g styrene a mixture of 1.2 g styrene and 0.6 g hexyl acetate was used. Hexyl acetate was then encapsulated in the polystyrene@SiO$_2$ core-shell nanocapsules. According to electron microscopy data, the size of the core-shell nanocapsules was ca. 150 nm.

Example 8

1.2 g docosane powder was added into 30 g of water of pH 7 at 60° C. After complete melting of docosane, 1.2 g polyethoxysiloxane was added. The mixture was then emulsified by means of sonication at 60° C. The resulting milky emulsion was gently stirred at 60° C. for 1 day. The obtained particles were isolated by centrifugation at 11000 rµm, rinsed 3 times with water, and then dried. According to electron microscopy data, the size of the core-shell nanoparticles and nanocapsules was ca. 480 nm and was narrowly distributed. The silica shell thickness was ca. 20 nm.

Example 9

1.2 g myristyl myristate was added into 30 g of water of pH 7 at 60° C. After complete melting of myristyl myristate, 1.2 g polyethoxysiloxane was added. The mixture was then emulsified using T 25 digital ULTRA-TURRAX® dispersion device (IKA) at 60° C. The resulting milky emulsion was gently stirred at 60° C. for 1 day. The resulting particles were isolated by centrifugation at 11000 rµm, rinsed 3 times with water, and then dried. According to electron microscopy data, the size of the core-shell particles was in the range from 4 to 8 µm.

Example 10

The synthetic route was similar to that described in Example 7, only instead of 1.2 g myristyl myristate 1.2 g of a mixture of myristyl myristate and octyl acetate (weight ratio 1:1) was used. This mixture was then encapsulated in SiO$_2$ capsules with a size ranging from 4 to 8 µm.

Example 11

1.5 g docosane was added into 30 g of water of pH 7 at 60° C. After complete melting of docosane, 1.5 g polyethoxysiloxane and 0.75 g PDMS with a viscosity of 10 cSt were added. The mixture was then emulsified by means of sonication under 60° C. The resulting milky emulsion was gently stirred at 60° C. for 1 day. The resulting capsules were isolated by centrifugation at 11000 rµm, rinsed 3 times with deionized water, and then dried. According to electron microscopy data, the size of the PDMS@docosane@SiO$_2$ capsules was ca. 960 nm and was narrowly distributed. The silica shell thickness was 20 nm.

Example 12

1.2 g polyethoxysiloxane, 1.2 g styrene, and 0.03 g AIBN were mixed to form a uniform and transparent oil phase. Then 0.24 g pure water was added into the oil phase and emulsified by means of sonication. The resulting milky water-in-oil emulsion was then emulsified in 30 g water of pH 7 using sonication. The obtained water-in-oil-in-water double emulsion was heated at 70° C. under nitrogen atmosphere for 24 h. The milky dispersion was centrifuged at 11000 rpm. The obtained white solid was rinsed several times with water to yield water@SiO$_2$@polystyrene@SiO$_2$ capsule particles. According to electron microscopy data, the size of the nanoparticles was ca. 200 nm and was narrowly distributed.

Example 13

The synthetic route was similar to that described in Example 11. Only 0.24 g pure water, which was encapsulated, was replaced by 0.24 g of a 5% (w/w) aqueous solution of glucose. Thus the glucose solution@SiO$_2$@polystyrene@SiO$_2$ capsules of ca. 200 nm were obtained.

Example 14

6 g docosane and 4 g polyethoxysiloxane were mixed together and heated to 60° C. After complete melting of docosane, 2 g of a 5% (w/w) aqueous solution of glucose were added. The system was emulsified by means of sonication under 60° C. The resulting water-in-oil emulsion was emulsified in 60 g water of pH 7 using T 25 digital ULTRA-TURRAX® dispersion device (IKA) at 60° C. The obtained water-in-oil-in-water double emulsion was heated at 60° C. for 24 h. The milky dispersion was cooled down to room temperature and centrifuged at 11000 rpm. The obtained white solid was rinsed several times with water to yield the glucose solution@SiO$_2$@docosane@SiO$_2$ capsules with a size ranging from 1 to 5 μm were obtained.

The invention claimed is:

1. A process for the preparation of silica-based micro- and nanocapsules loaded with up to 99% (w/w) hydrophobic organic compounds, comprising the step of:
    emulsifying a hydrophobic, water insoluble liquid comprising (i) polyalkoxysiloxane (PAOS) or amphiphilic PAOS that are partially substituted with hydrophilic groups and (ii) at least one hydrophobic organic liquid in an aqueous solution, without additional surfactants and without preformed (nano)particles, under shearing forces for a time period sufficient to form the silica-based capsules.

2. The process according to claim 1, wherein the at least one hydrophobic organic liquid is selected from alkanes, alkenes, alkynes, esters, ethers, ketones, aldehydes, aromatic compounds, polymers, etc.

3. The process according to claim 1, wherein PAOS is substituted with poly(ethylene glycol) monoalkyl ester of different molecular weight and different degrees of substitution.

4. A process for the preparation of silica-based micro- and nanocapsules loaded with up to 99% (w/w) hydrophobic, water insoluble polymers, comprising the steps of:
    a) emulsifying a hydrophobic, water insoluble solution comprising (i) polyalkoxysiloxane (PAOS), (ii) a hydrophobic liquid in an aqueous solution under shearing forces without additional surfactants and without preformed (nano)particles, where the hydrophobic liquid is a mixture of radically polymerizable organic monomers with an initiator; and
    b) heating the resulting emulsion to a higher temperature to induce the polymerization for a time period sufficient to form the silica-based capsules,
    c) cooling the mixture down to room temperature, and
    d) isolating the thus obtained polymer@SiO$_2$ capsules.

5. The process according to claim 4, wherein one or more non-(co)polymerizable hydrophobic organic compounds are additionally added to the reaction system in step a) to obtain hydrophobic organic compounds@polymer@SiO$_2$ capsules, wherein the non-polymerizable hydrophobic organic compounds are selected from alkanes, esters, ethers, ketones, aldehydes, aromatic compounds, or polymers that can turn into a liquid form at the emulsification temperature in step a).

6. A process for the preparation of silica-based micro- and nanocapsules loaded with up to 99% (w/w) an at room temperature crystallizable hydrophobic organic compound, comprising the steps of:
    a) emulsifying a hydrophobic, water insoluble solution comprising (i) polyalkoxysiloxane (PAOS) and (ii) a hydrophobic liquid in an aqueous solution under shearing forces without additional surfactants and without preformed (nano)particles, where the hydrophobic liquid is an at room temperature crystallizable, hydrophobic organic compound and the emulsification is carried out at a temperature above the melting temperature of this compound, and
    b) subsequently heating the emulsion obtained in step a) for a time period sufficient to form the silica-based capsules,
    c) cooling the mixture down to room temperature, and
    d) isolating the thus obtained crystallizable, hydrophobic organic compound@SiO$_2$ capsules.

7. The process according to claim 6, wherein the at room temperature crystallizable, hydrophobic organic compound is selected from waxes including alkanes, esters of alkyl alcohols and alkyl carboxylic acids, or their mixtures.

8. The process according to claim 6, wherein hydrophobic organic compounds are additionally added to the reaction system in step a) to obtain hydrophobic organic compounds@SiO$_2$ capsules, wherein the hydrophobic organic compounds are selected from alkanes, esters, ethers, ketones, aldehydes, aromatic compounds, or polymers that can turn into a liquid form at the emulsification temperature in step a).

9. A process for the preparation of silica-based micro- and nanocapsules loaded with up to 95% (w/w) hydrophilic, water soluble substances, comprising the steps of:
    a) emulsifying an aqueous solution containing hydrophilic, water soluble substances in a hydrophobic, water insoluble solution comprising (i) polyalkoxysiloxane (PAOS), (ii) radically polymerizable hydrophobic organic monomers and (iii) an initiator under shearing forces without additional surfactants and without preformed (nano)particles;
    b) emulsifying the water-in-oil emulsion of step a) in an aqueous solution under shearing forces without additional surfactants and without preformed (nano)particles;
    c) heating the emulsion to a higher temperature to induce the polymerization for a time period sufficient to form the silica-based capsules,
    d) cooling the mixture down to room temperature, and
    e) isolating the thus obtained silica-based capsules.

10. The process according to claim 9, wherein one or more non-polymerizable hydrophobic organic compounds are additionally added to the reaction system in step a) or b) to incorporate them into the organic phase of the capsules, wherein the non-polymerizable hydrophobic organic compounds are preferably selected from alkanes, esters, ethers, ketones, aldehydes, aromatic compounds, or polymers that can turn into a liquid form at the emulsification temperature in step a) and b).

11. A process for the preparation of silica-based micro- and nanocapsules loaded with up to 95% (w/w) hydrophilic, water soluble substances, comprising the steps of:
    a) emulsifying an aqueous solution containing hydrophilic, water soluble substances in a hydrophobic, water insoluble solution comprising (i) polyalkoxysiloxane (PAOS), (ii) molten organic compounds that crystallize at room temperature under shearing forces at a temperature above the melting temperature of the crystallizable organic material without additional surfactants and without preformed (nano)particles, b) emulsifying the water-in-oil emulsion of step a) in an aqueous solution at a temperature above the melting temperature of the crystallizable organic material without additional surfactants and without preformed (nano)particles, c) subsequently heating the emulsion obtained in step b) for a time period sufficient to form the silica-based capsules, d) cooling the mixture down to room temperature, and e) isolating the thus obtained silica-based capsules.

12. The process according to claim 11, wherein one or more hydrophobic organic compounds are additionally added to the reaction system in step a) or b) to incorporate them into the organic phase of the capsules, wherein the hydrophobic organic compounds are preferably selected from alkanes, alkenes, alkynes, esters, ethers, ketones, aldehydes, aromatic compounds, or polymers that can turn into a liquid form at the emulsification temperature in step a) and b).

13. The process according to claim 1, wherein polyethoxysiloxane is used as PAOS.

14. The process according to claim 4, wherein the radically polymerizable organic monomers are selected from styrene, methyl styrene, alkyl methacrylates, alkyl acrylates, acrylonitrile, or their mixtures.

15. The process according to claim 4, wherein the initiator is a thermal initiator including 2,2'-azobis(2-methylpropionitrile), 2,2'-azobis-(2,4-dimethylvaleronitrile), 2,2'-azobis-(2-methylbutyronitrile), benzoyl peroxide, or a photoinitiator.

* * * * *